United States Patent
Morikane et al.

(10) Patent No.: US 11,504,343 B2
(45) Date of Patent: Nov. 22, 2022

(54) AQUEOUS ADHESIVE

(71) Applicant: Dia Pharmaceutical Co., Ltd., Kashihara (JP)

(72) Inventors: Shinji Morikane, Kashihara (JP); Daizou Morikane, Kashihara (JP)

(73) Assignee: DIA PHARMACEUTICAL CO., LTD., Nara (JP)

( * ) Notice: Subject to any disclaimer, the term of this patent is extended or adjusted under 35 U.S.C. 154(b) by 465 days.

(21) Appl. No.: 16/499,919

(22) PCT Filed: Jul. 31, 2018

(86) PCT No.: PCT/JP2018/028571
§ 371 (c)(1),
(2) Date: Oct. 1, 2019

(87) PCT Pub. No.: WO2020/026329
PCT Pub. Date: Feb. 6, 2020

(65) Prior Publication Data
US 2021/0401767 A1    Dec. 30, 2021

(51) Int. Cl.
| | | |
|---|---|---|
| *A61K 9/70* | (2006.01) | |
| *A61K 31/196* | (2006.01) | |
| *A61K 47/02* | (2006.01) | |
| *A61K 47/12* | (2006.01) | |
| *A61K 47/14* | (2017.01) | |
| *A61K 47/26* | (2006.01) | |
| *A61K 47/32* | (2006.01) | |
| *A61K 47/38* | (2006.01) | |

(52) U.S. Cl.
CPC .......... *A61K 9/7061* (2013.01); *A61K 31/196* (2013.01); *A61K 47/02* (2013.01); *A61K 47/12* (2013.01); *A61K 47/14* (2013.01); *A61K 47/26* (2013.01); *A61K 47/32* (2013.01); *A61K 47/38* (2013.01)

(58) Field of Classification Search
CPC .... A61K 9/7061; A61K 31/196; A61K 47/02; A61K 47/12; A61K 47/14; A61K 47/26; A61K 47/32; A61K 47/38
See application file for complete search history.

(56) References Cited

U.S. PATENT DOCUMENTS 6,528,077 B1    3/2003    Syudo

FOREIGN PATENT DOCUMENTS

| | | |
|---|---|---|
| EP | 1151751 A1 | 11/2001 |
| JP | 11-139964 A | 5/1999 |
| JP | 2001-026540 A | 1/2001 |
| JP | 2001-064175 A | 3/2001 |
| JP | 2003-095929 A | 4/2003 |
| JP | 2009-155434 A | 7/2009 |
| WO | WO2001/013915 A1 | 3/2001 |

OTHER PUBLICATIONS

International Search Report (ISR) Relating to International Application No. PCT/JP2018/028571, dated Oct. 23, 2018.
Written Opinion of the ISA relating to International Application No. PCT/JP2018/028571, dated Oct. 23, 2018.

*Primary Examiner* — Robert A Wax
*Assistant Examiner* — Olga V. Tcherkasskaya
(74) *Attorney, Agent, or Firm* — Gavrilovich, Dodd & Lindsey LLP

(57) ABSTRACT

The present invention aims to provide an aqueous adhesive which has both good moldability and strong adhesive force to the skin, and provides good feeling when used. The present invention can provide an adhesive with good shape retention performance by formulating two or more aqueous macromolecules, polyhydric alcohols, aqueous and insoluble cross-linking agents.

9 Claims, 2 Drawing Sheets

Diagram of a cataplasm (patch)

AQUEOUS ADHESIVE

FIELD OF THE INVENTION

The present invention relates to an aqueous adhesive for use in cataplasm.

BACKGROUND OF THE INVENTION

A cataplasm is in structure of three layers including support, adhesive and release film (liner), as shown in FIG. 1.

In prior art, it has been problematic as follows and industrially difficult to coat uniformly an adhesive of aqueous substrate onto a ventilatable non-woven cloth while spreading it thinly. (1) When an adhesive is cross-linked, its gel intensity increases, so that it cannot be spread thinly. (2) If an adhesive is coated on a ventilatable non-woven cloth when cross-linked insufficiently, it exudes from the cloth.

Technology of SoL in GeL, as shown in FIG. 2, was developed by the present inventors to solve these problems of prior art.

With the SoL in GeL technology, gel is formed by dispersing aqueous macromolecules, wherein cross-linking points exist, in water and cross-linking them. In the matrix of three-dimensional structure formed by the cross-linking, uncross-linked aqueous macromolecules, polyhydric alcohols and hydrophobic components etc. are confined, so that release of drugs and water etc. is controlled.

Meanwhile, cooling performance and drug permeability are important for cataplasms. Regarding permeability of drugs, it is known that when water content in an adhesive attached to the skin is higher, its drug absorbency improves. However, when water content in an adhesive increases, its shape retention performance deteriorates, which easily causes exudation and extrusion from support. Therefore, as a countermeasure, in order to harden the adhesive and improve its shape retention performance, more cross-linking agents are needed. When the amount of cross-linking agents is increased, the adhesive becomes hard. However, at the same time, its adhesive force deteriorates, so that it loses its function as an adhesive, which is problematic. In order to compensate for the lost adhesive force, some thickener and/or tackifier are normally added. However, it may cause some defects such as rash and skin irritation due to the physical properties of the adhesive.

DISCLOSURE OF THE INVENTION

Problems that the Invention Aims to Solve

The present invention aims to solve the above problems and defects in prior art.

Means to Solve the Problems

As a result of intensive studies by the present inventors, it has been found that an adhesive with good shape retention performance can be provided by formulating two or more aqueous macromolecules, polyhydric alcohols, aqueous and insoluble cross-linking agents, so that the present invention is completed.

That is, the above problems have been solved by providing the following inventions.

(1) An adhesive comprising 60% or more of water, 3 to 15% of polyacrylic acid and/or partially neutralized product thereof or a salt thereof, 0.05 to 0.3% of aqueous and insoluble cross-linking agents, 3 to 30% or less of polyhydric alcohol and 0.01 to 3% of a pH adjuster.

(2) The adhesive according to (1), wherein the ratio of aqueous the cross-linking agent to the insoluble cross-linking agent is 1:1 to 1:300.

(3) The adhesive according to (1), wherein the ratio of the polyacrylic acid to the salt thereof is 1:99 to 3:2.

(4) The adhesive according to (1), wherein the polyhydric alcohol is glycerin or trimethylolpropane.

(5) The adhesive according to any one of (1) to (4), wherein the aqueous cross-linking agent is aluminum potassium sulfate and the insoluble cross-linking agent is dihydroxy aluminum amino acetate.

(6) The adhesive according to (1), which further comprises 1 to 10% of carboxyvinyl polymer and/or carboxymethylcellulose or a salt thereof and 1 to 10% of polyvinyl alcohol.

(7) The adhesive according to any one of (1) to (6), wherein the thickness of the adhesive is 0.1 to 10 mm.

(8) The adhesive according to any one of (1) to (7), wherein the gel intensity of the adhesive during coating is 100 g/50 cm2 or more.

(9) The adhesive according to any one of (1) to (7), wherein the gel intensity of the adhesive during coating is 120 to 250 g/50 cm2.

(10) The adhesive according to any one of (1) to (7), wherein the adhesive force of the adhesive is ball tack 26 or more.

(11) The adhesive according to any one of (1) to (7), wherein the adhesive force of the adhesive is ball tack 28 to 32.

(12) The adhesive according to any one of (1) to (7), wherein the normal gel intensity of the adhesive is 250 g/50 cm2 or more.

(13) The adhesive according to any one of (1) to (7), wherein the gel intensity of the adhesive during coating is 100 g/50 cm2 or more and adhesive force is ball tack 26 or more.

EMBODIMENT OF THE INVENTION

Figure 1:
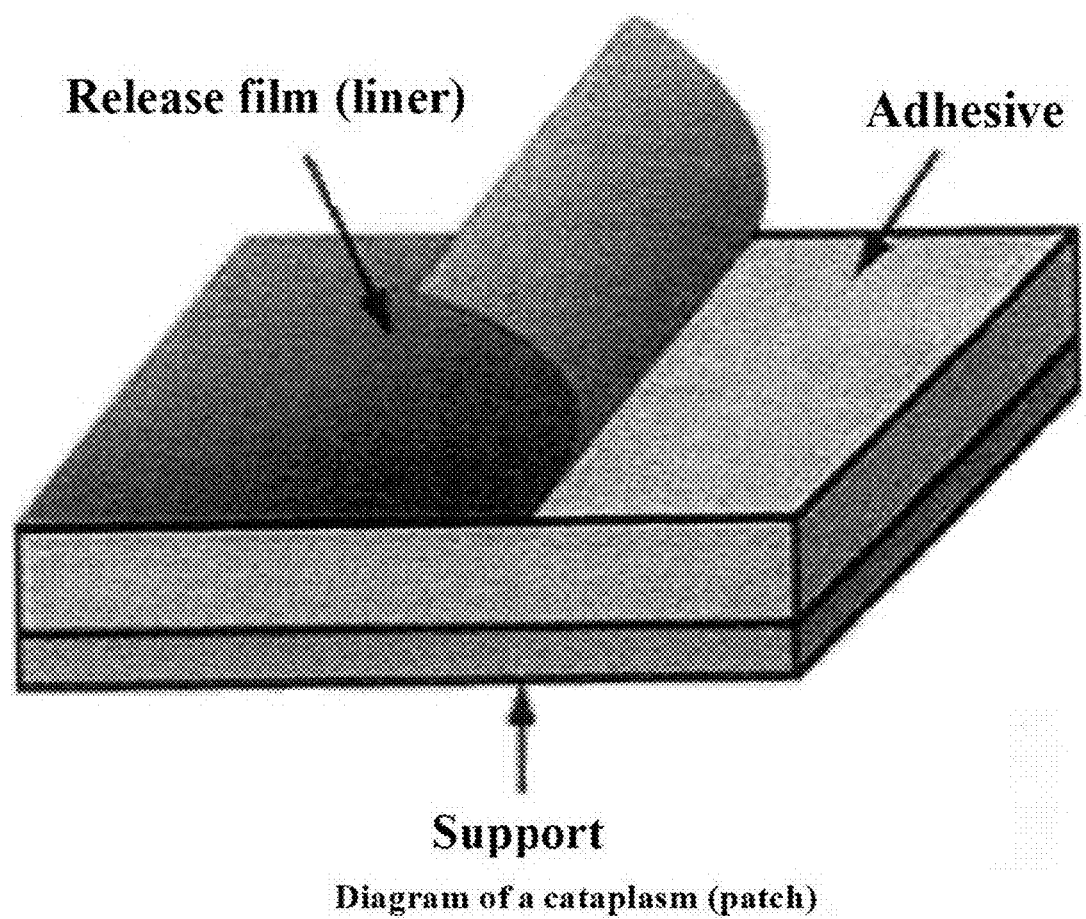
FIG. 1 shows a cataplasm is in structure of three layers including support, adhesive and release film (liner).
Figure 2:
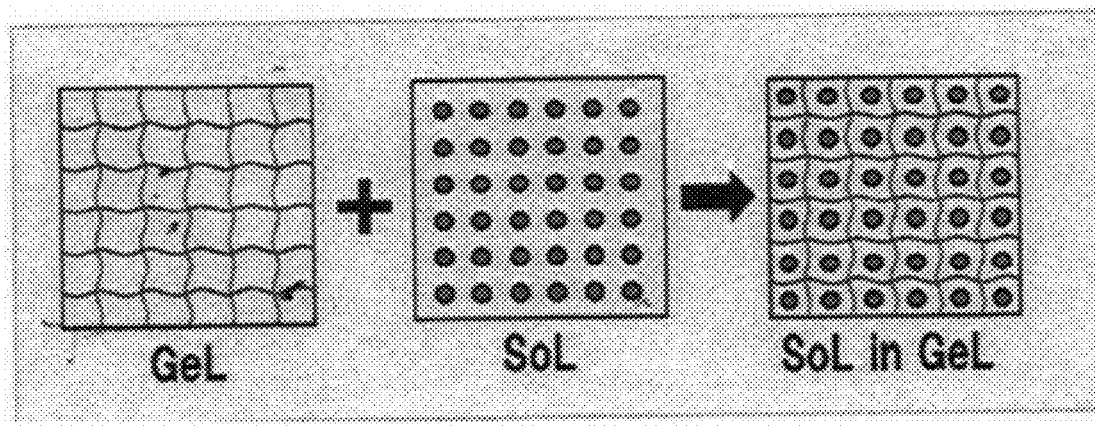
FIG. 2 shows technology of SoL in GeL was developed by the present inventors to solve these problems of prior art.

Unless otherwise stated, the terms used in the specification and claims have the meanings described below.

Water

The adhesive of the present invention comprises 60% by mass or more, preferably 70 to 85% by mass of water. When the water amount is in this range, water can be retained in the skin where the adhesive is attached.

Aqueous Macromolecular Compounds

The aqueous macromolecular compounds used in present invention are not especially limited. They can be occasionally selected. Their examples include polyacrylic acid and the like, such as polyacrylic acid or sodium polyacrylate etc., polyacrylic acid, a partially neutralized product thereof or a salt thereof, gelatin, polyvinyl alcohol, polyvinyl pyrrolidone, carboxyvinyl polymer, carboxy methylcellulose or a salt thereof, hydroxypropylcellulose, hydroxyethylcellulose, methylcellulose, sodium alginate, xanthan gum, arabia gum, tragacanth gum, karaya gum and anhydride maleic copolymer etc. Polyacrylic acid or its partially neutralized product, sodium polyacrylate, carboxyvinyl polymer, carboxymethylcellulose or its salt, polyvinyl alcohol etc. are preferable. It is preferable to use two or more of the aqueous macromolecular compounds in combination. By the way, the said "aqueous" in the present invention refers to dissolution in water at a concentration of 1% by mass or more.

Contents of the aqueous macromolecular compounds are not especially limited. They can be occasionally selected.

The contents based on the total composition for adhesive layer added with water and other optional additives are shown below as examples.

When polyacrylic acid and/or its partially neutralized product, and its salt are used as the aqueous macromolecular compounds, their contents are preferably 3 to 15% by mass, and more preferably 5 to 10% by mass.

When carboxyvinyl polymer and/or carboxymethylcellulose or salts thereof are used as the aqueous macromolecular compounds, their contents are preferably 1 to 10% by mass, and more preferably 2 to 5% by mass.

When polyvinyl alcohol is used as the aqueous macromolecular compound, its content is preferably 10% by mass or less, and more preferably 3 to 8% by mass.

Cross-Linking Agents

As cross-linking agents, multivalent metal compounds are used.

Adhesive force of a patch to the skin can be adjusted by adding a cross-linking agent, which reacts with aqueous macromolecular compounds. If the adhesive force is improved, effect of reducing the pain felt when a patch is peeled away from the skin can be achieved. In addition, change in viscosity of a coating solution for non-aqueous adhesive layer is inhibited during its preparation, so that coating performance on liner or support is improved. Besides, patch productivity can also be improved.

Examples of multivalent metal compounds used in the present invention include magnesium compounds, calcium compounds, zinc compounds, aluminum compounds, titanium compounds, tin compounds, iron compounds, manganese compounds, cobalt compounds and nickel compounds etc., among which aluminum compounds, magnesium compounds and calcium compounds are preferable from the viewpoint of safety to the skin.

Any of these aluminum compounds, calcium compounds and magnesium compounds can be used properly.

Specifically, one or more selected from aluminum hydroxide, aluminum sulfate, ammonium aluminum sulfate, aluminum potassium sulfate, aluminum chloride, aluminum lactate, dihydroxy aluminum amino acetate (aluminum glycinate), aluminum acetate, synthetic aluminum silicate, aluminum metasilicate; calcium sulfate, calcium nitrate, calcium chloride, calcium acetate, calcium oxide; magnesium hydroxide, magnesium carbonate, magnesium sulfate, magnesium acetate, magnesium oxide, alumina/magnesium hydroxide, magnesium aluminometasilicate, magnesium aluminosilicate, synthetic hydrotalcite, and aqueous or insoluble compounds of their double salts containing these metal atoms can be used. In addition, antacids containing aluminum or magnesium can also be formulated as multivalent metal salts.

From the viewpoints of adhesive force of patch to the skin and its productivity, combinations of aqueous multivalent metal compounds with insoluble multivalent metal compounds, particularly the combination of aluminum potassium sulfate with dihydroxy aluminum amino acetate, are preferable.

The amount of multivalent metal compounds formulated is preferably 0.01 to 1 portion by mass, and more preferably 0.05 to 0.3 portion by mass based on 100 portions by mass of the total composition for the adhesive layer added with water and other optional additives. By formulating in a larger amount than the lower limit of this range, the performance of cross-linking with aqueous macromolecular components is improved. The shape retention performance is maintained. Besides, the pain felt when a patch is peeled away from the skin is further reduced.

On the other hand, by formulating in a smaller amount than the higher limit of this range, cross-linking with aqueous macromolecular components is appropriately controlled. The adhesive force of the patch to the skin is further improved.

Polyhydric Alcohols

The polyhydric alcohols are not limited. They can be occasionally selected. Their examples include dihydric alcohols, trihydric alcohols, tetrahydric alcohols, pentahydric alcohols and hexahydric alcohols.

Examples of the dihydric alcohols include polyethylene glycol, ethylene glycol, propylene glycol, 1,3-butylene glycol, diethylene glycol, dipropylene glycol and 1,3-hexylene glycol etc. Examples of the trihydric alcohols include glycerin and trimethylolpropane etc. Examples of the tetrahydric alcohols include erythritol, pentaerythritol and diglycerin etc. Examples of the pentahydric alcohols include xylitol etc. Examples of the hexahydric alcohols include sorbitol and dipentaerythritol etc. Trihydric alcohols, particularly glycerin, are preferable polyhydric alcohols.

The amount of polyhydric alcohols formulated is preferably 30 weight % or less, and more preferably 5 to 15 weight %, based on the total components for the adhesive layer added with polyhydric alcohols, water and other optional additives. If a larger amount of polyhydric alcohols is used, when gel-like adhesive is coated to support and cures to form an adhesive layer, the curing speed may slow down.

pH Adjusters

A pH adjuster promotes metal ion elution from multivalent metal compounds. At the same time, it functions as a pH controller for the composition that forms adhesive layer. Examples of pH adjusters include tartaric acid, lactic acid and citric acid etc., among which tartaric acid is especially preferable.

The pH adjusters can be used alone or in combination of two or more. With regard to the amount of the pH adjusters to be used, it is preferable that when water, a polyhydric alcohol and other optional additives etc. are added to form a composition of adhesive layer, the pH value of the composition falls into the range of 3 to 7. The amount of pH adjusters used is preferably 0.01 to 3% by mass based on 100 portions by mass of total composition for the adhesive layer added with water, polyhydric alcohol and other optional additives.

The adhesive of the present invention is preferably molded as thin as 0.1 to 10 mm, as long as the adhesive does not peel off during use due to its dryness and its reduce in adhesive force to the skin by its cracks, etc.

In the present invention, when an adhesive is coated, the gel intensity during the coating is 100 g/50 cm2 or more, preferably 120 to 250 g/50 cm2, wherein the said "gel intensity during the coating" refers to the intensity of an adhesive in which no exudation or extrusion occurs when the adhesive is coated in shape of a sheet and applied by mass on the sheet immediately thereafter (within 0 to 30 minutes).

The adhesive force of the adhesive of the present invention is ball tack 26 or more, preferably ball tack 28 to 32.

The normal gel intensity of the adhesive of the present invention is 250 g/50 cm2 or more, preferably 300 g/50 cm2 or more, wherein the said "normal gel intensity" refers to the gel intensity of an adhesive which has sufficiently hardened when its cross-linking has progressed 3 days or longer after manufacture.

The aqueous adhesive of the present invention may be used to remove local heat or as a supporter. Besides, it can also be formulated with pharmacologically active ingredients. Unlimited examples of pharmacologically active ingredients include anti-inflammatory agents, such as glycol salicylate, methyl salicylate, alclofenac, anphenac sodium, ufenamate, spurophen, bufexamac, anpiroxicam, piroxicam, meloxicam, indomethacin, ketoprofen, zaltoprofen, sulindac, tenoxicam, acetaminophen, mefenamic acid, flufenamic acid, ibuprofen, loxoprofen, pranoprofen, fenbufen, diclofenac, diclofenac sodium, oxyphenbutazone, felbinac and flurbiprofen etc. which are nonsteroidal antiinflammatory drugs and amcinonide, prednisolone valerate acetate, diflucortolone valerate, dexamethasone valerate, betamethasone valerate, diflorazone acetate, dexamethasone acetate, hydrocortisone acetate, methylprednisolone acetate, diflupredonato, betamethasone dipropionate, dexamethasone, triamcinolone acetonide, harcinonide, flumetasone pivalate, budesonide, mometasone furoate, fluocinonide, fluocinolone acetonide, fludroxiocortide, prednisolone, alclomethasone propionate, clobetasol propionate, dexamethasone propionate, deprodone propionate, beclomethasone propionate, betamethasone, clobetasone butyrate, hydrocortisone butyrate, hydrocortisone butyrate propionate and betamethasone butyrate propionate, which are steroidal antiinflammatory drugs; antifungal agents, such as croconazole hydrochloride, neticonazole hydrochloride, clotrimazole, ketoconazole, isoconazole nitrate, econazole nitrate, oxonazole nitrate, sulconazole nitrate, miconazole nitrate, thioconazole, bifonazole and ranoconazole etc.; anti-urinary incontinence agents, such as oxybutynin hydrochloride, telodiline hydrochloride and flavoxate hydrochloride etc.; muscle relaxants, such as eperisone hydrochloride, afroquarone, chlorphenesine carbamate, tizanidine hydrochloride, tolperisone hydrochloride, oxazolam, flurazepam hydrochloride, diazepam, prazepam, flunitrazepam, flurazepam, brotizolam, bromazepam, chlorzoxazone, fenprobamate, methocarbamol, dantrolene sodium and pridinol mesilate etc.; antispasmodic agents, such as butyl scopolamine bromide, atropine sulfate and papaverine hydrochloride etc.; cardiac stimulants, such as nitroglycerin and isosorbide dinitrate etc.; smoking cessation agents, such as nicotine etc.; anti-allergic drugs, such as azelastine hydrochloride, epinastine hydrochloride, oxatomide, seratrodast, tranilast and ketotifen fumarate etc.; local anesthetics, such as procaine hydrochloride, dibucaine hydrochloride and lidocaine etc.; disinfectants, such as iodine, iodine tincture, iodoform and povidone iodine etc.; skin stimulating agents, such as capsaicin, red pepper extract and nonylic acid amide etc. Pharmacologically active ingredients can be used alone or in combination of two or more, if necessary.

Moreover, additives which are usually formulated into aqueous adhesives can be formulated in the aqueous adhesive of the present invention. For example, cross-linking rate modifier, such as chelators like edetate sodium and sodium metaphosphate etc.; organic acids like lactic acid, citric acid and tartaric acid etc. and their metal salts; inorganic acids like sulfuric acid and hydrochloric acid etc.; organic bases like diethylamine, diethanolamine, triethanolamine and diisopropanolamine etc.; inorganic bases like sodium hydroxide and ammonia etc.; fillers, such as kaolin, titanium, light anhydrous silica and hydrophobic light anhydrous silica etc.; antioxidants, such as sulfites like anhydrous sodium sulfite, sodium bisulfite, sodium pyrosulfite, sodium thiosulfate, rongalite, sodium edetate, dibutylhydroxytoluene and dibutylhydroxyanisole etc. can be formulated. Besides, surfactants, perfumes and preservatives etc. can also be formulated, if necessary.

Manufacturing methods for the aqueous adhesive of the present invention are not particularly limited. Conventional manufacturing methods for aqueous adhesives are used. For example, when used as an aqueous patch, the above essential components and other necessary components are mixed with water and kneaded thoroughly to form a uniform paste. Then, it is spread on support such as paper, woven cloth, non-woven cloth and plastic film etc. and coated with polyethylene film etc., if necessary.

EXAMPLES

The present invention will be further illustrated in detail by using following examples. However, it is not limited to these examples.

Example 1

Into a stirrer, 3 portions by weight of polyacrylic acid, 5 portions by weight of sodium polyacrylate, 0.15 portion by weight of dihydroxy aluminum amino acetate, 0.02 portion by weight of aluminum potassium sulfate, 0.1 portion by weight of 1-menthol, 10 portions by weight of glycerin, 50 portions by weight (5 portions by weight as polyvinyl alcohol) of 10% aqueous solution of polyvinyl alcohol prepared previously, 1 portion by weight of carboxyvinyl polymer, 1 portion by weight of sodium carboxymethylcellulose, 0.1 portion by weight of pH adjuster (tartaric acid), 0.1 portion by weight of preservative (methyl paraben) and 0.1 portion by weight of surfactant (polyoxyethylene sorbitan monooleate (20E.O) were charged. Then, purified water was added to reach 74.43% as target water content in the adhesive. The mixture was stirred at 30 rpm for 15 minutes to give an adhesive. The adhesive was coated to non-woven cloth to make 3000 g, 2000 g, 1000 g and 500 g/1 m², respectively, which were then bonded with polyethylene film, as release film, and cut into pieces in sizes of 14 cm×5 cm and 5 cm×10 cm, as products.

Examples 2 to 9 and Comparative Examples 1 to 11

In examples 2 to 9 and comparative examples 1 to 11, products were manufactured in the same way as that in example 1 by charging all specified components into a stirrer and stirring at 30 rpm for 15 minutes. Following tests were conducted with the products of these examples and comparative examples to assess various performance Test 1 Coating Performance Coating performance was evaluated when the products were coated as thin as 3000 g and 500 g/1 m². Those which could be coated uniformly were assessed at "○". Those which could be coated but not uniformly were assessed at "Δ". Those which could not be coated because the adhesive was too hard, or those which could not be coated continuously because the adhesive was too soft so that it exuded, extruded or fell back from non-woven cloth were assessed at "x".

Test 2 Evaluation of Shape Retention Performance

If shape retention performance is poor, even if the manufacturing can be conducted and no exudation or extrusion occurs immediately afterwards, the adhesive may exude on side of non-woven cloth or may extrude from between the non-woven cloth and polyethylene film due to its own weight or surface tension etc. Accordingly, the product was coated as thin as 2000 g/l m² and cut into sheets in size of 5 cm×10 cm. Each sheet was sealed separately in an aluminum bag to prevent water volatilization. The products were let stand for 0.5 hour or 1 month and observed to confirm if any exudation or extrusion occurred or not. The assessment was conducted at n=5. Those wherein no exudation or extrusion occurred in any of the five sheets were assessed at "○". Those wherein exudation or extrusion occurred in 1 or 2 sheets were assessed at "Δ". Those wherein exudation or extrusion occurred in 3 or more sheets were assessed at "x".

Test 3 Evaluation of Gel Intensity During Coating Immediately after Manufacture

If the gel intensity is strong, the adhesive becomes hard. Accordingly, it is difficult to coat an adhesive into shape of a thin sheet, so that it is difficult to manufacture. On the other hand, if the gel intensity is weak, and the adhesive is soft, it is easy to mold it into shape of a sheet. However, when pressure is applied, exudation and extrusion may occur. Moreover, if a product has insufficient gel intensity, its release film (liner) cannot be peeled away. In addition, when two or more sheets are put in piles, exudation or extrusion may occur. Moreover, when being used, adhesive remains on the skin where attached, which causes quality problems. In order to avoid this problem, multiple sheets cannot be stacked, or they should be put in a partition or a case to prevent pressure on the sheets, etc., which results in poor productivity and increased cost. Instead of immediate processing, they are left standing for about a week after manufacture, or heated to warm up. It is necessary to wait until cross-linking is proceeded and the gel intensity has increased before completing the manufacture, which results in poor production efficiency. Neither too weak nor too strong gel intensity during coating is preferable. If the value immediately after manufacture is 100 g/50 cm² or less, exudation or extrusion occurs easily during handling. If the value is 120 g/50 cm² or more, no extrusion occurs even if about 10 sheets are stacked, which is preferable for easy handling. In addition, when the value of gel intensity is 250 g/50 cm² or more, the adhesive becomes difficult to be coated thinly. In this test, the products were cut into sheets in size of 5 cm×10 cm. The sheets were applied with pressure of 10 to 300 g/50 cm² before being left to stand for 24 hours. The gel intensity (pressure resistance) wherein no exudation or extrusion occurred was assessed. The test was conducted at n=5. The lowest pressure at which exudation or extrusion occurred was recorded. Those wherein no exudation or extrusion occurred even at the pressure of 300 g/50 cm² were recorded as "300 g<".

Test 4 Evaluation of Temporal Gel Intensity

In the case where the gel intensity is 200 g/50 cm² or less, the adhesive cannot be peeled away from the release film. Besides, the sheet that cannot be easily peeled away stretches, which causes problems when used. Therefore, the gel intensity is more preferably 220 g/50 cm² or more. It cannot be used as a product unless its gel intensity is 200 g/50 cm² or more. In order to increase gel intensity, although heating may be conducted, it is desirable to let it stand still to increase its gel intensity rapidly from the viewpoint of productivity. In this test, products were coated as thin as 2000 g/l m² and cut into sheets in size of 5 cm×10 cm. Each sheet was put into an aluminum bag and sealed before it was let to stand. After 3 days or 1 month, the sheet was taken out and applied with pressure of 10 to 300 g (per 50 cm²) before being left to stand for 24 hours. The gel intensity (pressure resistance) that would cause no exudation or extrusion was assessed. The test was conducted at n=5. The lowest pressure at which exudation or extrusion occurred was recorded. Those wherein no exudation or extrusion occurred even at the pressure of 300 g were recorded as "300 g<".

Test 5 Evaluation of Adhesive Force

For evaluation of adhesive force, the method of inclined ball tack testing (6.12.3.2) described in the Japanese Pharmacopoeia, 17th edition (JP17) was used. The assessment was conducted using the rolling ball tack method. Regarding the adhesive force, when the value of ball tack is 20 or less, the adhesive peels off or gradually slips off from pasting point. Accordingly, the value of ball tack is preferably 26 or more, desirably 28 to 32 or more. In this test, products obtained immediately after manufacture and those obtained after the accelerated test (40° C., 6 months) were assessed. The test was conducted at n=5. The minimum value of ball tack was recorded as adhesive force.

Test 6 Evaluation of Peeling Performance

Each of the sheets in the size of 10 cm×14 cm which had been coated at 1000 g/l m² was put in an aluminum bag and sealed before being let to stand. One month after manufacture, the sheets were attached to 5 persons for 5 hours. Pain felt when the sheets were peeled away was assessed. Those which could be peeled away without any problem and pain were assessed at "○". Those from which 1 or 2 persons felt pain when peeled away, or which remained on the skin were assessed at "Δ". Those from which 3 or more persons felt pain when peeled away, or which remained on the skin were assessed at "x".

Test 7 Evaluation of Water Retention Time

The water content in sheets affects drug release and cooling performance on pasting point. Meanwhile, cooling performance is achieved from graduate water vaporization. Water content decreases while the water in sheets gets lost gradually. As the function of sheets, if the water retention time is longer, the water content in sheets can be maintained for a longer time, which results in persistent drug release and cooling performance. The test was conducted at n=3. Sheets in size 5 cm×10 cm which had been coated as thin as 2000 g/l m² was pasted on a hot plate of 30° C. under humidity of 50%. The sheet weight was recorded every 30 minutes from the start of the test. Since the weight decreased gradually due to water volatilization, the point when change in the weight ceased (the average value of the change in weight at n=3 was ±0.02 g or less) was recorded as water retention time.

Evaluation of Prior Art

With products of examples 1 to 8, the tests were conducted, in which good results were obtained. In comparative example 1, products were manufactured in which water content was adjusted to 44%. The gel intensity during coating immediately after the manufacture was 50 g/50 cm². It was easy to be coated. However, when mass of 60 g/50 cm² or more was applied, exudation occurred. In addition, on day 3 after the manufacture, normal gel intensity could not be obtained, for which reason, its productivity was poor. Besides, regarding the change in adhesive force, the value of ball tack after accelerated testing turned to 21, while it was 32<on day 3 after the manufacture. Remarkable decline in adhesive force was observed. Moreover, in comparative example 2, products were manufactured without using any aqueous cross-linking agent, and by formulating purified water in the large amount of 74.3%. The gel intensity was not sufficient. Exudation and extrusion from non-woven cloth occurred during the manufacturing, which caused difficulty in the manufacture process. In the evaluation test on exudation/extrusion, exudation occurred in all products one month after the manufacture. Moreover, regarding the change in adhesive force, the value of ball tack after accelerated testing turned to 22, while it was 32<on day 3 after the manufacture. Similar with that in comparative example 1, remarkable decline in adhesive force was observed. In addition, regarding the feeling when the products were used, skin residue was found. The result of assessment was "inappropriate". In comparative example 3, the total amount of polyacrylic acid formulated was 1.5%. The adhesive was too soft to be coated or molded into shape of a sheet. The amounts of components formulated in examples 1 to 8 and comparative examples 1 to 3 are shown in Table 1. The test results are shown in Table 2.

TABLE 1

| Formulation | | Examples | | | | | |
|---|---|---|---|---|---|---|---|
| | | 1 | 2 | 3 | 4 | 5 | 6 |
| A. polyacrylic acid and the like | polyacrylic acid | 3.00% | 1.00% | | 3.00% | 3.00% | 3.00% |
| | sodium polyacrylate | 5.00% | | | | 2.00% | |
| | partially neutralized product of polyacrylic acid | | 8.00% | 10.00% | 5.00% | 5.00% | 5.00% |
| B. cross-linking agent | insoluble cross-linking agent (dihydroxy aluminum acetate) | 0.150% | 0.15% | 0.100% | | 0.200% | 0.150% |
| | insoluble cross-linking agent (aluminum hydroxide) | | | | 0.200% | | |
| | aqueous cross-linking agent (aluminum potassium sulfate) | 0.020% | 0.020% | 0.020% | 0.010% | 0.005% | 0.020% |
| | aqueous cross-linking agent (aluminum sulfate) | | | | | | |
| C. polyhydric alcohol | glycerin | 10.00% | 10.00% | 10.00% | 10.00% | | |
| | propylene glycol | | | | | 5.00% | |
| | 1,3-butylene glycol | | | | | 5.00% | |
| | D-sorbitol | | | | | | 5.00% |
| | syrup of reduced maltose | | | | | | 5.00% |
| D. aqueous macromolecule | polyvinyl alcohol | 5.00% | 5.00% | 5.00% | 5.00% | 5.00% | 5.00% |
| E. | carboxyvinyl polymer | 1.00% | 1.00% | 1.00% | 0.50% | 1.00% | 1.00% |
| | sodium carboxymethylcellulose | 1.00% | 1.00% | 1.00% | 0.50% | 1.00% | |
| | gelatin | | | | | | 1.00% |
| F. pH adjuster | tartaric acid | 0.10% | 0.10% | 0.10% | 0.10% | 0.10% | 0.10% |
| preservative | methylparaben | 0.10% | 0.10% | 0.10% | 0.10% | 0.10% | 0.10% |
| surfactant | polysorbate 80 | 0.10% | 0.10% | 0.10% | 0.10% | 0.10% | 0.10% |
| | active ingredient: menthol | 0.10% | 0.10% | 0.10% | 0.10% | 0.10% | 0.10% |
| water | purified water | 74.43% | 73.43% | 72.48% | 75.39% | 72.40% | 74.43% |

| Formulation | | Examples | | Comparative examples | | |
|---|---|---|---|---|---|---|
| | | 7 | 8 | 1 | 2 | 3 |
| A. polyacrylic acid and the like | polyacrylic acid | 1.00% | 0.50% | 3.00% | 3.00% | 0.50% |
| | sodium polyacrylate | 3.00% | | 5.00% | 5.00% | 1.00% |
| | partially neutralized product of polyacrylic acid | | 2.50% | | | |
| B. cross-linking agent | insoluble cross-linking agent (dihydroxy aluminum acetate) | 0.180% | 0.200% | 0.300% | 0.300% | 0.150% |
| | insoluble cross-linking agent (aluminum hydroxide) | | | | | |
| | aqueous cross-linking agent (aluminum potassium sulfate) | 0.020% | 0.05% | | | 0.02% |
| | aqueous cross-linking agent (aluminum sulfate) | | | | | |
| C. polyhydric alcohol | glycerin | 8.00% | | 30.00% | 10.00% | 10.00% |
| | propylene glycol | | 2.50% | 10.00% | | |
| | 1,3-butylene glycol | | | | | |
| | D-sorbitol | | | | | |
| | syrup of reduced maltose | | | | | |
| D. aqueous macromolecule | polyvinyl alcohol | 3.00% | 3.00% | 5.00% | 5.00% | 5.00% |
| E. | carboxyvinyl polymer | 0.50% | 0.10% | 1.00% | 1.00% | 1.00% |
| | sodium carboxymethylcellulose | 0.50% | 0.50% | 1.00% | 1.00% | 1.00% |
| | gelatin | | | | | |

TABLE 1-continued

| | | | | | | |
|---|---|---|---|---|---|---|
| F. pH adjuster | tartaric acid | 0.10% | 0.10% | 0.10% | 0.10% | 0.10% |
| preservative | methylparaben | 0.10% | 0.10% | 0.10% | 0.10% | 0.10% |
| surfactant | polysorbate 80 | 0.10% | 0.10% | 0.10% | 0.10% | 0.10% |
| | active ingredient: menthol | 0.10% | 0.10% | 0.10% | 0.10% | 0.10% |
| water | purified water | 83.40% | 90.25% | 44.30% | 74.30% | 80.93% |

TABLE 2

| Formulation | | Examples | | | | | | | | Comparative examples | | |
|---|---|---|---|---|---|---|---|---|---|---|---|---|
| | | 1 | 2 | 3 | 4 | 5 | 6 | 7 | 8 | 1 | 2 | 3 |
| pH test | pH (4.5-6.5) | 4.8 | 5.0 | 5.5 | 4.8 | 4.7 | 4.8 | 4.5 | 5.0 | 4.8 | 4.7 | 4.9 |
| Test 1 Coating performance | amount of adhesive: 500 g/m² | ○ | ○ | ○ | ○ | ○ | ○ | ○ | ○ | ○ | ○ | ○ |
| | amount of adhesive: 3000 g/m² | ○ | ○ | ○ | ○ | ○ | ○ | ○ | ○ | ○ | ○ | ○ |
| Test 2 Evaluation of shape retention performance | exudation from non-woven cloth (during manufacture) | ○ | ○ | ○ | ○ | ○ | ○ | ○ | ○ | ○ | Δ | x |
| | exudation and extrusion from non-woven cloth (1 month after manufacture) | ○ | ○ | ○ | ○ | ○ | ○ | ○ | ○ | ○ | x | — |
| Test 3 Evaluation of gel intensity during coating immediately after manufacture | gel intensity during coating (immediately after manufacture) | 180 | 180 | 170 | 170 | 170 | 180 | 150 | 150 | 50 | 50 | — |
| Test 4 Evaluation of temporal gel intensity | normal gel intensity (on day 3 after manufacture) | 250 | 260 | 250 | 250 | 260 | 250 | 240 | 240 | 120 | 120 | — |
| | normal gel intensity (1 month after manufacture) | 300< | 300< | 300< | 300< | 300< | 300< | 300< | 300< | 300< | 300< | — |
| Test 5 Evaluation of adhesive force | value of ball tack (adhesive force) on day 3 after manufacture | 32< | 32< | 32< | 32< | 32< | 32< | 32< | 32< | 32< | 32< | — |
| | temporal value of ball tack (adhesive force) at 40° C. after 6 months | 31 | 31 | 31 | 31 | 32< | 31 | 31 | 30 | 21 | 22 | — |
| Test 6 Evaluation of peeling performance | Evaluation of peeling performance | ○ | ○ | ○ | ○ | ○ | ○ | ○ | ○ | ○ | x | x |
| Test 7 Evaluation of water retention time | water retention time | 10 | 10 | 9.5 | 10 | 10 | 10.5 | 11 | 12 | 4 | 10 | — |

Evaluation of Performance of Cross-Linking Agents Affected by their Type and Amount Tests were conducted with products of example 1 and comparative examples 4 to 8. In comparative examples 4 and 5, products were manufactured without using any aqueous cross-linking agent. As a result, exudation occurred both at the time of the manufacture and one month later. Besides, skin residue was found in the evaluation test of release, so that they were assessed at "inappropriate". In comparative examples 6, 7 and 8, products were manufactured without using any insoluble cross-linking agent. As a result, in comparative example 6, the products could be manufactured. However, exudation occurred one month later. Moreover, in comparative examples 7 and 8, the adhesive over cured and could not be coated into shape of a sheet as thin as 500 g and 3000 g/l m2. Accordingly, evaluations could not be conducted except pH test. It can be seen from the above results that when water content is high, an appropriate adhesive cannot be obtained if either insoluble or aqueous cross-linking agent is used alone. The amounts of components formulated in the example and comparative examples are shown in Table 3. The test results are shown in Table 4.

TABLE 3

| Formulation | | Example | Comparative examples | | | | |
|---|---|---|---|---|---|---|---|
| | | 1 | 4 | 5 | 6 | 7 | 8 |
| A. polyacrylic acid and the like | polyacrylic acid | 3.00% | 3.00% | 3.00% | 3.00% | 3.00% | 3.00% |
| | sodium polyacrylate | 5.00% | 5.00% | 5.00% | 5.00% | 5.00% | 5.00% |

TABLE 3-continued

|  |  | Example | Comparative examples | | | | |
|---|---|---|---|---|---|---|---|
| Formulation |  | 1 | 4 | 5 | 6 | 7 | 8 |
| B. cross-linking agent | insoluble cross-linking agent (dihydroxy aluminum acetate) | 0.150% | 0.300% | 0.150% |  |  |  |
|  | aqueous cross-linking agent (aluminum potassium sulfate) | 0.020% |  |  | 0.020% | 0.050% | 0.100% |
| C. polyhydric alcohol | glycerin | 10.00% | 10.00% | 10.00% | 10.00% | 10.00% | 10.00% |
| D. aqueous macromolecule | polyvinyl alcohol | 5.00% | 5.00% | 5.00% | 5.00% | 5.00% | 5.00% |
| E. | carboxyvinyl polymer | 1.00% | 1.00% | 1.00% | 1.00% | 1.00% | 1.00% |
|  | sodium carboxymethylcellulose | 1.00% | 1.00% | 1.00% | 1.00% | 1.00% | 1.00% |
| F. pH adjuster | tartaric acid | 0.10% | 0.10% | 0.10% | 0.10% | 0.10% | 0.10% |
| preservative | methylparaben | 0.10% | 0.10% | 0.10% | 0.10% | 0.10% | 0.10% |
| surfactant | polysorbate 80 | 0.10% | 0.10% | 0.10% | 0.10% | 0.10% | 0.10% |
|  | active ingredient: menthol | 0.10% | 0.10% | 0.10% | 0.10% | 0.10% | 0.10% |
| water | purified water | 74.43% | 74.30% | 74.45% | 74.58% | 74.55% | 74.50% |

TABLE 4

|  |  | Example | Comparative examples | | | | |
|---|---|---|---|---|---|---|---|
| Formulation |  | 1 | 4 | 5 | 6 | 7 | 8 |
| pH test | pH (4.5-6.5) | 4.8 | 4.7 | 4.9 | 4.8 | 4.7 | 4.8 |
| Test 1 Coating performance | amount of adhesive: 500 g/m² | ○ | ○ | ○ | ○ | x | x |
|  | amount of adhesive: 3000 g/m² | ○ | ○ | ○ | ○ | Δ | x |
| Test 2 Evaluation of shape retention performance | exudation from non-woven cloth (during manufacture) | ○ | Δ | x | ○ | ○ | — |
|  | exudation and extrusion from non-woven cloth (1 month after manufacture) | ○ | x | — | x | ○ | — |
| Test 3 Evaluation of gel intensity during coating immediately after manufacture | gel intensity during coating (immediately after manufacture) | 180 | 50 | 30 | 70 | 250 | — |
| Test 4 Evaluation of temporal gel intensity | normal gel intensity (on day 3 after manufacture) | 250 | 120 | 90 | 100 | 300< | — |
|  | normal gel intensity (1 month after manufacture) | 300< | 300< | 300< | 150 | 300< | — |
| Test 5 Evaluation of adhesive force | value of ball tack (adhesive force) on day 3 after manufacture | 32< | 32< | 32< | 32< | 28 |  |
|  | temporal value of ball tack (adhesive force) at 40° C. after 6 months | 31 | 22 | 31 | 32< | 24 | — |
| Test 6 Evaluation of peeling performance | Evaluation of peeling performance | ○ | x | x | x | ○ | x |
| Test 7 Evaluation of water retention time | water retention time | 10 | 10 | 10 | 10 | 9 | — |

Effect of Aqueous Macromolecules

Tests were conducted with products of example 1 and comparative examples 9 and 10. As a result, regarding tests 1 to 5, difference from example 1 was not found either in comparative examples 9 or 10. However, regarding test 6 of evaluation of peeling performance, the adhesives were attached to the skin. Pain was confirmed as a result when they were peeled away. Regarding test 7, water retention time decreased. The amounts of components formulated in the example and comparative examples are shown in Table 5. The test results are shown in Table 6.

TABLE 5

| Formulation |  | Example 1 | Comparative example 9 | Comparative example 10 |
|---|---|---|---|---|
| A. polyacrylic acid and the like | polyacrylic acid | 3.00% | 3.00% | 3.00% |
|  | sodium polyacrylate | 5.00% | 5.00% | 5.00% |
| B. cross-linking agent | insoluble cross-linking agent (dihydroxy aluminum acetate) | 0.150% | 0.150% | 0.150% |
|  | aqueous cross-linking agent (aluminum potassium sulfate) | 0.020% | 0.020% | 0.020% |

TABLE 5-continued

| Formulation | | Example 1 | Comparative example 9 | Comparative example 10 |
|---|---|---|---|---|
| C. polyhydric alcohols | glycerin | 10.00% | 15.00% | 12.00% |
| D. aqueous macromolecule | polyvinyl alcohol | 5.00% | | 5.00% |
| E. | carboxyvinyl polymer | 1.00% | 1.00% | |
| | sodium carboxymethylcellulose | 1.00% | 1.00% | |
| F. pH adjuster | tartaric acid | 0.10% | 0.10% | 0.10% |
| preservative | methylparaben | 0.10% | 0.10% | 0.10% |
| surfactant | polysorbate 80 | 0.10% | 0.10% | 0.10% |
| | active ingredient: menthol | 0.10% | 0.10% | 0.10% |
| water | purified water | 74.43% | 74.43% | 74.43% |

TABLE 6

| Formulation | | Example 1 | Comparative example 9 | Comparative example 10 |
|---|---|---|---|---|
| pH test | pH (4.5-6.5) | 4.8 | 4.8 | 4.8 |
| Test 1 Coating performance | amount of adhesive: 500 g/m² | ○ | ○ | ○ |
| | amount of adhesive: 3000 g/m² | ○ | ○ | ○ |
| Test 2 Evaluation of shape retention performance | exudation from non-woven cloth (during manufacture) | ○ | ○ | ○ |
| | exudation and extrusion from non-woven cloth (1 month after manufacture) | ○ | ○ | ○ |
| Test 3 Evaluation of gel intensity during coating immediately after manufacture | gel intensity during coating (immediately after manufacture) | 180 | 150 | 150 |
| Test 4 Evaluation of temporal gel intensity | normal gel intensity (on day 3 after manufacture) | 250 | 240 | 250 |
| | normal gel intensity (1 month after manufacture) | 300< | 300< | 300< |
| Test 5 Evaluation of adhesive force | value of ball tack (adhesive force) on day 3 after manufacture | 32< | 32< | 32< |
| | temporal value of ball tack (adhesive force) at 40° C. after 6 months | 31 | 31 | 31 |
| Test 6 Evaluation of peeling performance | Evaluation of peeling performance | ○ | Δ | Δ |
| Test 7 Evaluation of water retention time | water retention time | 10 | 6 | 7 |

Evaluation of Products Containing Active Pharmaceutical Ingredients

Figure 3:
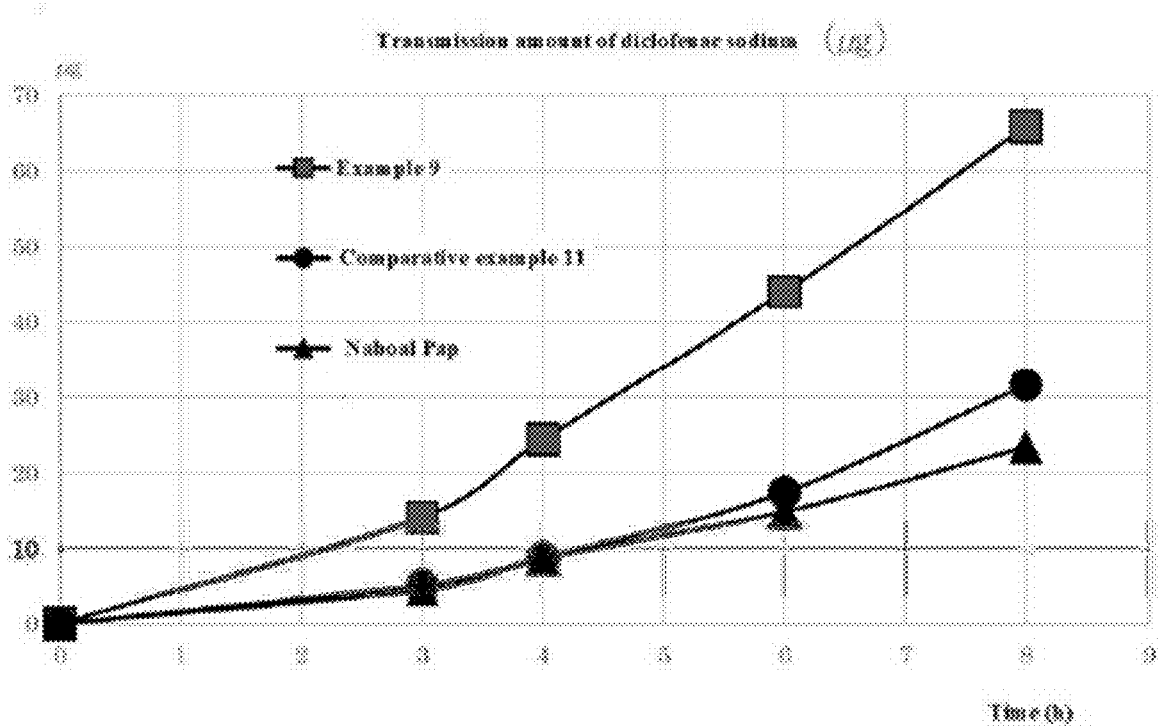
FIG. 3 shows the results of drug permeation tests with products in example 9 and comparative example 11 and commercially available Naboal Pap (Lot. 03006A), using diclofenac sodium, were conducted at n=6 with a Franz cell.

Using diclofenac, drug permeation tests with products in example 9 and comparative example 11 and commercially available Naboal Pap (Lot. 03006A) were conducted at n=6 with a Franz cell. The vertical diffusion cell method (6.13.3) described in the Japanese Pharmacopoeia, 17th edition (JP17) was used in permeability test. As a result, the amount of diclofenac sodium permeated in example 9 was about 3 times larger compared with those of comparative example 11 wherein the water content was decreased, and the commercial product. The amounts of components formulated in example 9 and comparative example 11 are shown in Table 7. The results of the permeability test are shown in Table 8 and FIG. 3.

TABLE 7

| Formulation | | Example 9 | Comparative example 11 | Comparative example 12 |
|---|---|---|---|---|
| A. polyacrylic acid and the like | polyacrylic acid | 1.50% | 1.50% | Naboal Pap |
| | sodium polyacrylate | 5.70% | 5.70% | |
| B. cross-linking agent | insoluble cross-linking agent (dihydroxy aluminum acetate) | 0.120% | 0.120% | |
| | aqueous cross-linking agent (aluminum potassium sulfate) | 0.020% | 0.020% | |
| C. polyhydric alcohol | glycerin | 7.00% | 30.00% | |
| | 1,3-butylene glycol | 7.00% | 7.00% | |
| D. aqueous macromolecule | polyvinyl alcohol | 3.00% | 3.00% | |

TABLE 7-continued

| Formulation | | Example 9 | Comparative example 11 | Comparative example 12 |
|---|---|---|---|---|
| E. | carboxyvinyl polymer | | 0.00% | 0.00% |
|  | sodium carboxymethylcellulose | | 1.00% | 1.00% |
| F. pH adjuster | tartaric acid | | 0.20% | 0.20% |
| preservative | methylparaben | | 0.10% | 0.10% |
| surfactant | polysorbate 80 | | 0.20% | 0.20% |
| solvent | N-methyl pyrrolidone | | 3.00% | 3.00% |
|  | active ingredient: diclofenac sodium | | 1.00% | 1.00% |
| water | purified water | | 70.16% | 47.16% |

TABLE 8

(µg)

| | Time (h) | | | | |
|---|---|---|---|---|---|
| Samples | 0 | 3 | 4 | 6 | 8 |
| Example 9 | 0 | 14.17 | 24.41 | 44 | 65.9 |
| Comparative example 11 | 0 | 5.13 | 8.74 | 17.51 | 31.61 |
| Naboal Pap | 0 | 4.5 | 8.74 | 14.94 | 23.43 |

What is claimed is:

1. An adhesive in a form of a gel comprising no less than 60% by mass of water, 3 to 15% by mass of polyacrylic acid and/or partially neutralized product thereof or a salt thereof, 0.05 to 0.3% by mass of aqueous and insoluble cross-linking agents, wherein a ratio of the aqueous cross-linking agent to the insoluble cross-linking agent is 1:5 to 1:40, 3 to 30% by mass of polyhydric alcohol and 0.01 to 3% by mass of a pH adjuster, and wherein the aqueous cross-linking agent is aluminum potassium sulfate and the insoluble cross-linking agent is dihydroxy aluminum amino acetate or aluminum hydroxide, and wherein a gel intensity of the adhesive during coating is 100 g/50 cm$^2$ or more and an adhesive force of the adhesive is ball tack 26 or more.

2. The adhesive according to claim 1, wherein a ratio of the polyacrylic acid to the salt thereof is 1:99 to 3:2.

3. The adhesive according to claim 1, wherein the polyhydric alcohol is glycerin or trimethylolpropane.

4. The adhesive according to claim 1, wherein the aqueous cross-linking agent is aluminum potassium sulfate and the insoluble cross-linking agent is dihydroxy aluminum amino acetate.

5. The adhesive according to claim 1, which further comprises 1 to 10% by mass of carboxyvinyl polymer and/or carboxymethylcellulose or a salt thereof and 1 to 10% by mass of polyvinyl alcohol.

6. The adhesive according to claim 1, wherein a thickness of the adhesive is 0.1 to 10 mm.

7. The adhesive according to claim 1, wherein the gel intensity of the adhesive during coating is 120 to 250 g/50 cm$^2$.

8. The adhesive according to claim 1, wherein the adhesive force of the adhesive is ball tack 28 to 32.

9. The adhesive according to claim 1, wherein a normal gel intensity of the adhesive is 250 g/50 cm$^2$ or more.

* * * * *